United States Patent
Anspach, III et al.

(10) Patent No.: US 9,566,058 B2
(45) Date of Patent: *Feb. 14, 2017

(54) ANCHOR/SUTURE USED FOR MEDICAL PROCEDURES

(71) Applicant: DePuy Synthes Products, Inc., Raynham, MA (US)

(72) Inventors: William E. Anspach, III, Stuart, FL (US); Eddy H. del Rio, Royal Palm Beach, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 75 days.

This patent is subject to a terminal disclaimer.

(21) Appl. No.: 14/223,234

(22) Filed: Mar. 24, 2014

(65) Prior Publication Data
US 2014/0288596 A1 Sep. 25, 2014

Related U.S. Application Data

(60) Continuation of application No. 11/542,445, filed on Oct. 3, 2006, now Pat. No. 8,696,703, which is a
(Continued)

(51) Int. Cl.
*A61B 17/04* (2006.01)
*A61F 2/08* (2006.01)

(52) U.S. Cl.
CPC ......... *A61B 17/0401* (2013.01); *A61F 2/0811* (2013.01); *A61B 17/0487* (2013.01);
(Continued)

(58) Field of Classification Search
CPC ............... A61B 2017/0401; A61B 2017/0409; A61B 2017/0411; A61B 2017/0414; A61B 2017/0427; A61B 2017/0446; A61B 2017/0451; A61B 2017/0459; A61B 17/0401; A61B 17/0487; A61F 2/0811; A61F 2002/0823; A61F 2002/0817

See application file for complete search history.

(56) References Cited

U.S. PATENT DOCUMENTS 4,738,255 A 4/1988 Goble et al.
4,750,492 A 6/1988 Jacobs
(Continued)

FOREIGN PATENT DOCUMENTS

WO 2007147634 12/2007

OTHER PUBLICATIONS

International Preliminary Report on Patentability, dated May 22, 2007, in International Application No. PCT/US2005/026091.
(Continued)

*Primary Examiner* — Tuan V Nguyen
(74) *Attorney, Agent, or Firm* — Meunier Carlin & Curfman LLC

(57) ABSTRACT

For suture tying in a medical procedure including the use of an anchor that includes a suture locking device that includes a sliding pin guided by axial side slots formed in the locking device that forces the suture where the two ends thereof are inserted into the interior of the suture locking mechanism to drive the captured suture and pin to fit into a recess on the top of the suture locking mechanism such that the top of the pin binds the suture against the upper inner surface of the recess. The recess can be serrated to enhance the locking capability and the pin is polygonal shaped to provide side surfaces that run parallel to the wall of the recess to assure that the side portion of the pin does not fracture the suture and cause it to weaken. The locking of the suture is automatic upon the deployment of the anchor which actuates the pin into the locking position, thus eliminating the necessity of manually knotting the suture and improving the cinching
(Continued)

of the tissue to the bone. The suture locking mechanism is usable for attaching tissue to the bone, tying tissue to tissue and the like. The disclosure also includes the method of deploying the combined anchor and suture locking device in a medical procedure.

4 Claims, 7 Drawing Sheets

Related U.S. Application Data division of application No. 10/989,786, filed on Nov. 16, 2004, now Pat. No. 7,144,415.

(52) U.S. Cl.
CPC ............... *A61B 2017/0409* (2013.01); *A61B 2017/0412* (2013.01); *A61B 2017/0414* (2013.01); *A61B 2017/0437* (2013.01); *A61B 2017/0454* (2013.01); *A61B 2017/0456* (2013.01); *A61B 2090/037* (2016.02); *A61F 2002/0888* (2013.01)

(56) References Cited

U.S. PATENT DOCUMENTS

| | | |
|---|---|---|
| 5,013,316 A | 5/1991 | Goble et al. |
| 5,100,417 A | 3/1992 | Cerier et al. |
| 5,156,616 A | 10/1992 | Meadows et al. |
| 5,383,905 A | 1/1995 | Golds et al. |
| 5,456,685 A | 10/1995 | Huebner |
| 5,472,452 A | 12/1995 | Trott |
| 5,492,442 A | 2/1996 | Lasner |
| 5,571,139 A | 11/1996 | Jenkins, Jr. |
| 5,584,835 A | 12/1996 | Greenfield |
| 5,645,589 A | 7/1997 | Li |
| 5,690,649 A | 11/1997 | Li |
| 5,702,397 A | 12/1997 | Goble et al. |
| 5,725,541 A | 3/1998 | Anspach et al. |
| 5,728,136 A | 3/1998 | Thal |
| 5,741,300 A | 4/1998 | Li |
| 5,766,250 A | 6/1998 | Cheritz et al. |
| 5,814,071 A | 9/1998 | McDevitt et al. |
| 5,843,087 A | 12/1998 | Jensen et al. |
| 5,843,127 A | 12/1998 | Li |
| 5,891,168 A | 4/1999 | Thal |
| 5,902,321 A | 5/1999 | Caspari et al. |
| 5,931,840 A | 8/1999 | Goble et al. |
| 5,948,000 A | 9/1999 | Larson et al. |
| 5,948,001 A | 9/1999 | Larsen |
| 5,957,953 A | 9/1999 | DiPoto et al. |
| 5,968,044 A | 10/1999 | Nicholson et al. |
| 6,022,373 A | 2/2000 | Li |
| 6,045,574 A | 4/2000 | Thal |
| 6,086,608 A | 7/2000 | Ek et al. |
| 6,129,762 A | 10/2000 | Li |
| 6,143,017 A | 11/2000 | Thal |
| 6,149,669 A | 11/2000 | Li |
| 6,156,039 A | 12/2000 | Thal |
| 6,200,329 B1 | 3/2001 | Fung et al. |
| 6,221,107 B1 | 4/2001 | Steiner et al. |
| 6,231,606 B1 | 5/2001 | Graf et al. |
| 6,290,711 B1 | 9/2001 | Caspari et al. |
| 6,328,758 B1 | 12/2001 | Tornier et al. |
| 6,524,317 B1 | 2/2003 | Ritchart et al. |
| 6,524,328 B2 | 2/2003 | Levinson |
| 6,527,794 B1 | 3/2003 | McDevitt et al. |
| 6,569,188 B2 | 5/2003 | Grafton et al. |
| 6,616,665 B2 | 9/2003 | Grafton et al. |
| 6,660,008 B1 | 12/2003 | Foerster et al. |
| 6,689,135 B2 | 2/2004 | Enayati |
| 6,692,516 B2 | 2/2004 | West, Jr. et al. |
| 6,730,092 B2 | 5/2004 | Songer |
| 6,770,076 B2 | 8/2004 | Foerster |
| 6,923,824 B2 | 8/2005 | Morgan et al. |
| 7,090,690 B2 | 8/2006 | Foerster et al. |
| 7,144,413 B2 | 12/2006 | Wilford et al. |
| 7,144,415 B2 | 12/2006 | Del Rio et al. |
| 7,713,286 B2 | 5/2010 | Singhatat |
| 8,696,703 B2 * | 4/2014 | Anspach, III ...... A61B 17/0401 606/232 |
| 2004/0133239 A1 | 7/2004 | Singhatat |
| 2005/0177165 A1 | 8/2005 | Zang et al. |
| 2006/0106422 A1 | 5/2006 | Del Rio et al. |
| 2008/0275469 A1 | 11/2008 | Fanton et al. |
| 2009/0281580 A1 | 11/2009 | Emannuel |
| 2009/0292321 A1 | 11/2009 | Collette |

OTHER PUBLICATIONS

Written Opinion, dated Mar. 6, 2011, in International Application No. PCT/US2005/026091.

International Search Report, dated Mar. 6, 2006, in International Application No. PCT/US2005/026091.

* cited by examiner

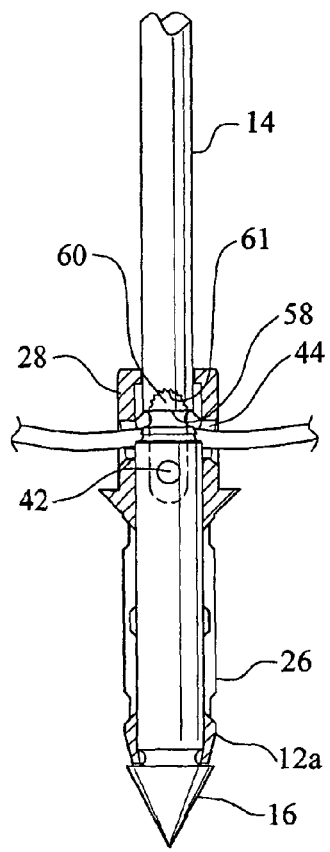 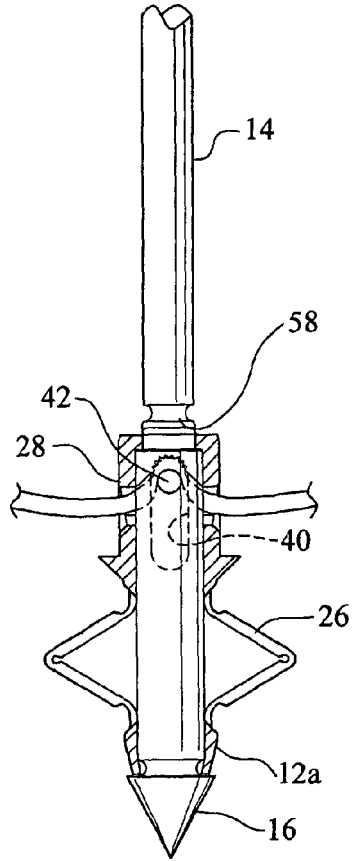 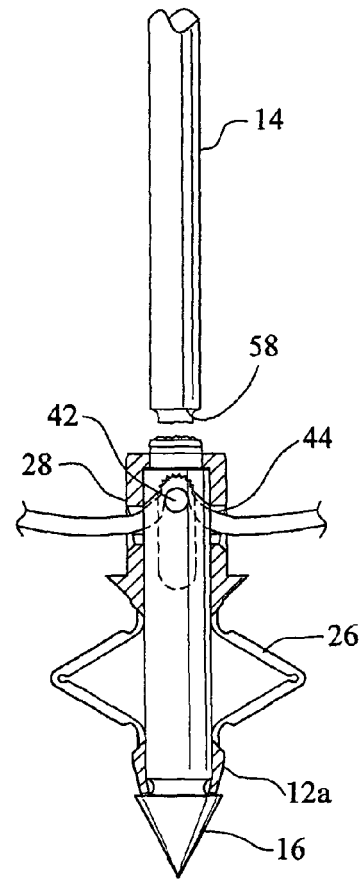
FIG. 5A        FIG. 5B        FIG. 5C
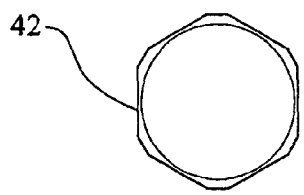
FIG. 6

ANCHOR/SUTURE USED FOR MEDICAL PROCEDURES

RELATED APPLICATIONS

This Application claims priority to U.S. application Ser. No. 11/542,445 (now U.S. Pat. No. 8,696,703), filed on Oct. 3, 2006, entitled "Anchor/suture used for medical procedures," which is a divisional application of U.S. patent application Ser. No. 10/989,786 (now U.S. Pat. No. 7,144,415), filed on Nov. 16, 2004. Both of these applications are herein incorporated by reference in their entirety.

TECHNICAL FIELD

This invention relates to anchors and sutures utilized in medical procedures and particularly to a combined suture lock and anchor adapted to adhere a tendon, muscle or tissue to the bone of the patient.

BACKGROUND OF THE INVENTION

As is well known by those skilled in the medical technology, knot tying of sutures when done in a medical procedure, as for example, when tying tissue to the bone, is deemed to be one of the weakest links in the procedure being performed by the surgeon. This is the case whether the procedure is arthroscopic or a partial or full opening of the area being repaired. It is well known in this technology that no two arthroscopic knots on the suture that are made by surgeons are the same and equally known is that a well known problem is that the surgeon cannot tie the knot in such a manner that the securing of the tissue to the bone is at its optimum. In other words, the tissue when tied down does not hug or cling to the bone as well as it could.

While this invention has been conceived in addressing rotator cuff tears with the purpose of obtaining a suture that solves the knot problem that is alluded to in the above paragraph, it will become obvious in the description of this invention that follows, that the inventive instrument can be utilized in other surgical procedures. The rotator cuff tear is quite common and because of the difficulty of tying the tissue to the bone this has presented an ever increasing problem to the surgeon. The rotator cuff is a group of muscles that attach, through their tendons, to the top of the upper arm bone (humerus). A tear in these tissues often require surgery to repair the tear. The options left to the surgeon, depending on the severity of the tear, is either an arthroscopic repair, a mini-open repair that combines arthroscopy and a small incision or open surgery. Whatever the procedure, the tissue is ultimately tied to the bone and often by use of an anchor that is secured into the bone and a suture that is tied to the tissue and anchor and then knotted. This invention is directed to a unique apparatus that secures the tissue to the bone and is judiciously adjusted so that the tissue is tied to the bone cinching to the bone as closely as is possible. Hence, this invention relates to an instrument that is used for tying tissue to the bone and to an instrument that automatically secures the suture and to the method for permitting the surgeon to manipulate the suture when utilizing this inventive apparatus in such a manner that the tissue will be cinched to the bone as close as it possibly can.

This instrument and method of shoulder repair is entirely different from the AutoCuff System made by Opus Medical which utilizes the SmartStitch Suturing Device and the Magnum Knotless Fixation Implant. This suturing device eliminates the knot tying by using a mechanized mattress stitch. The device places the stitch directly into the tissue. Once the stitch is placed in the cuff, the surgeon loads and deploys the Magnum Knotless Implant. This procedure is distinguishable from the present invention.

SUMMARY OF THE INVENTION

An object of this invention is to provide an improved apparatus for tying and locking the ends of suture that is used in a medical procedure.

A feature of this invention is to provide a suture locking device that includes a pin that is inserted in a hollow cylindrical body that is translated axially toward a wall internally in the body and providing apertures in the hollow cylindrical body where both reaches of the suture are threaded and the pin is moved upwardly to be urged against the wall so as to squeeze the suture reaches between the pin and the wall. Axial slots are formed in the side wall of the body and serve to guide the pin as it traverses axially in the body A recess is formed in the body and defines a wall that is contoured to complement the pin. The top surface of the recess is contoured into jutting surfaces or serrated and the pin is polygonal shaped where it includes flat surfaces that are oriented parallel to the side walls of the recess. The outer diameter of the cylinder may have opposing flats where the apertures are located and the holes allow the suture to be threaded through the body so that the reaches of the suture lie between the pin and the wall.

A still further object of this invention is to affix the suture locking device to a state-of-the-art anchor and modifying the frangible shaft of the anchor to include a drilled hole to accept the pin. A heretofore known tool resembling a gun is used to place the anchor into the bone. The actuation of the gun causes the pin to travel into the recess to squeeze the reaches of the suture and lock them in place.

An object of this invention is to provide a method used in a medical procedure for placing the anchor into the bone while the surgeon is pulling the suture reaches through the aperture of the suture locking device of this invention and simultaneously deploying the anchor to cinch the tissue to the bone surface. The surgeon threads the suture through the tissue and then into one aperture formed in the body and then through the hollow of the body and through the diametrically opposing aperture to lie one of the reaches between the pin and the serrated wall and then threading the other reach of the suture to diametrically opposed apertures formed in the body so that it also is placed between the pin and serrated wall.

The foregoing and other features of the present invention will become more apparent from the following description and accompanying drawings.

BRIEF DESCRIPTION OF THE DRAWINGS

FIGS. 5A, 5B and 5C are views in section and side elevation illustrating the operation of the suture/anchor of this invention from the insertion of the suture, the insertion of the anchor into the bone and the working shaft being broken in the final step of the operation of this invention;

FIG. 6 is an end view of the pin of this invention depicted in FIGS. 3-5C;

DETAILED DESCRIPTION OF THE INVENTION

As mentioned in the above paragraphs while this invention was conceived for tying sutures in a medical procedure dealing with the rotator cuff of a patient, as one skilled in this art will appreciate, this invention may have application for other medical procedures, including, but not limited to, not only for tying tissue to bone, but tying tissue to tissue and the like, so long as the tool for inserting the anchor into the body part has the capability of activating the suture locking device or a like tool is used without the anchor.

Figure 1:
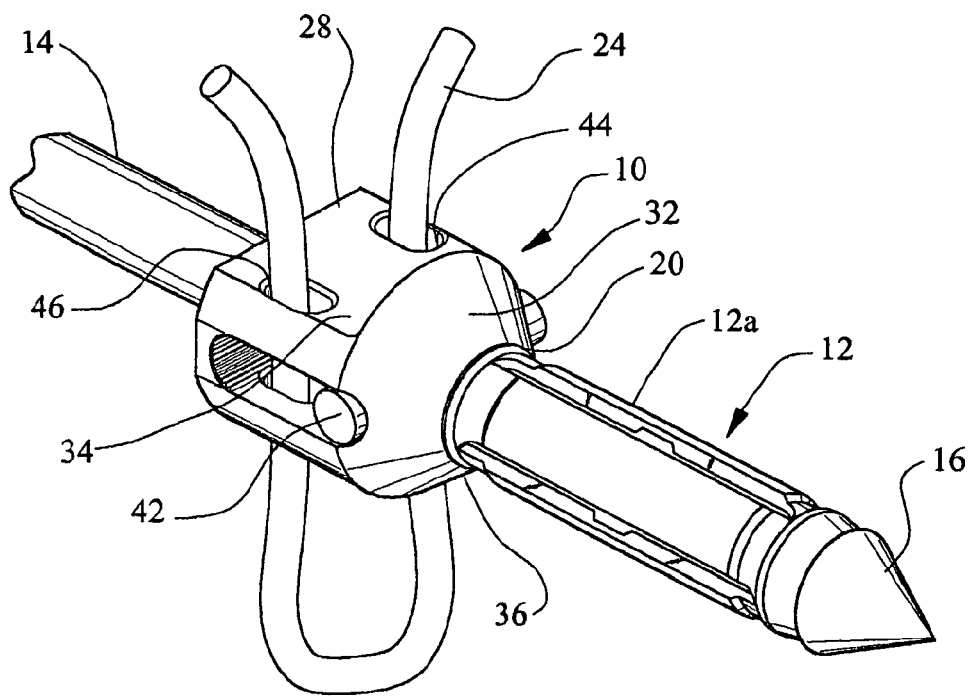
FIG. 1 is a perspective partial view illustrating the details of this invention when in the readied condition.
Figure 2:
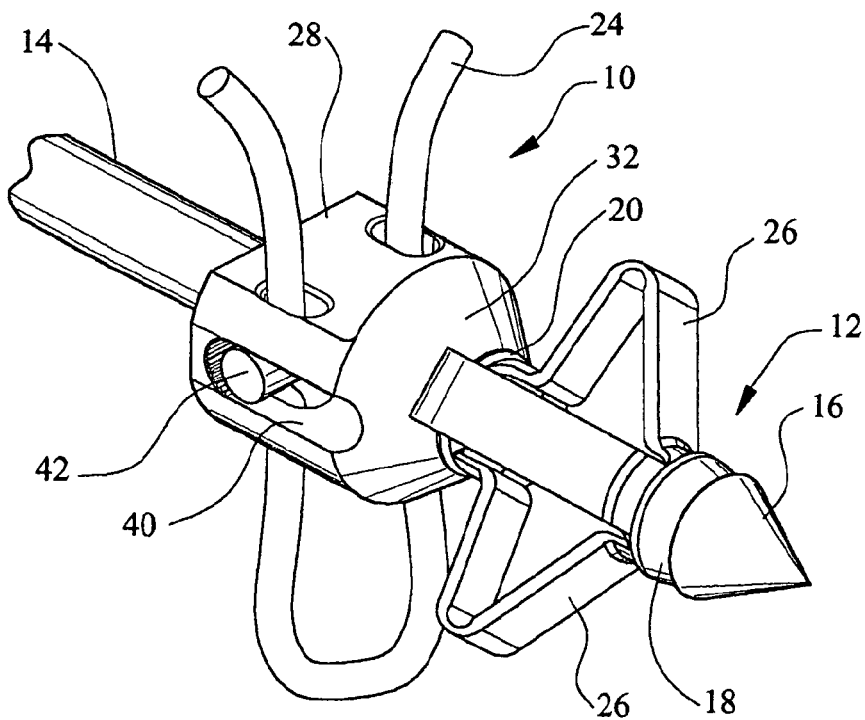
FIG. 2 is a fragmentary perspective view of the apparatus depicted in FIG. 1 illustrating the deployed position.

As best seen in FIGS. 1 and 2 the inventive suture locking device generally illustrated by reference numeral 10 is affixed to a well known anchor 12 of the type that includes a frangible shaft 14 (modified to accommodate the present invention, terminating at the distal end into a pointed end 16 (FIG. 9) and the flexible portion 14*a* which is comprised of annular bottom annular portion 18, flexible arms or wings 26 and a top annular portion 20 that mates with or made integral with the suture locking device 10. When deployed, the wings 26 of the anchor 12 flex as shown and operate much like a molly bolt and is forced into the bone structure to secure the anchor in place. In the heretofore anchor, the suture 24 would be threaded through the tissue 30 and through an aperture formed in the anchor (not shown) and the ends of the suture 24 would be knotted in a well known manner by the surgeon. Obviously, as detailed above, since the knot is made by the surgeon, it is difficult for the surgeon to both tie the suture and at the same time force the tissue to cling adjacent to the surface of the bone. As will be described in more detail hereinbelow the suture locking device 10 of this invention essentially ties and locks the suture in place and solves this problem.

Referring back to FIGS. 1 & 2, (like parts are numbered the same in all the Figs.) the present invention consist of the main hollow body 28 that is generally cylindrical in shape and being tapered at the end portion 32 flaring toward the anchor 12 and suitably attached or integrally formed therewith. The side surfaces 34 and 36 may be flattened as shown therein. Diametrically opposed elongated grooves 40 on either side of the main body 28 are formed on the non-flattened surface serve to guide pin 42 when it is translated axially for securing the suture as will be more fully described hereinbelow. Formed on the side of the main body 28 at the flattened surfaces are a pair of diametrically opposed apertures 44 and 46 that allow the suture to pass through the body 28 over the pin 42.

Figures 3, 4:
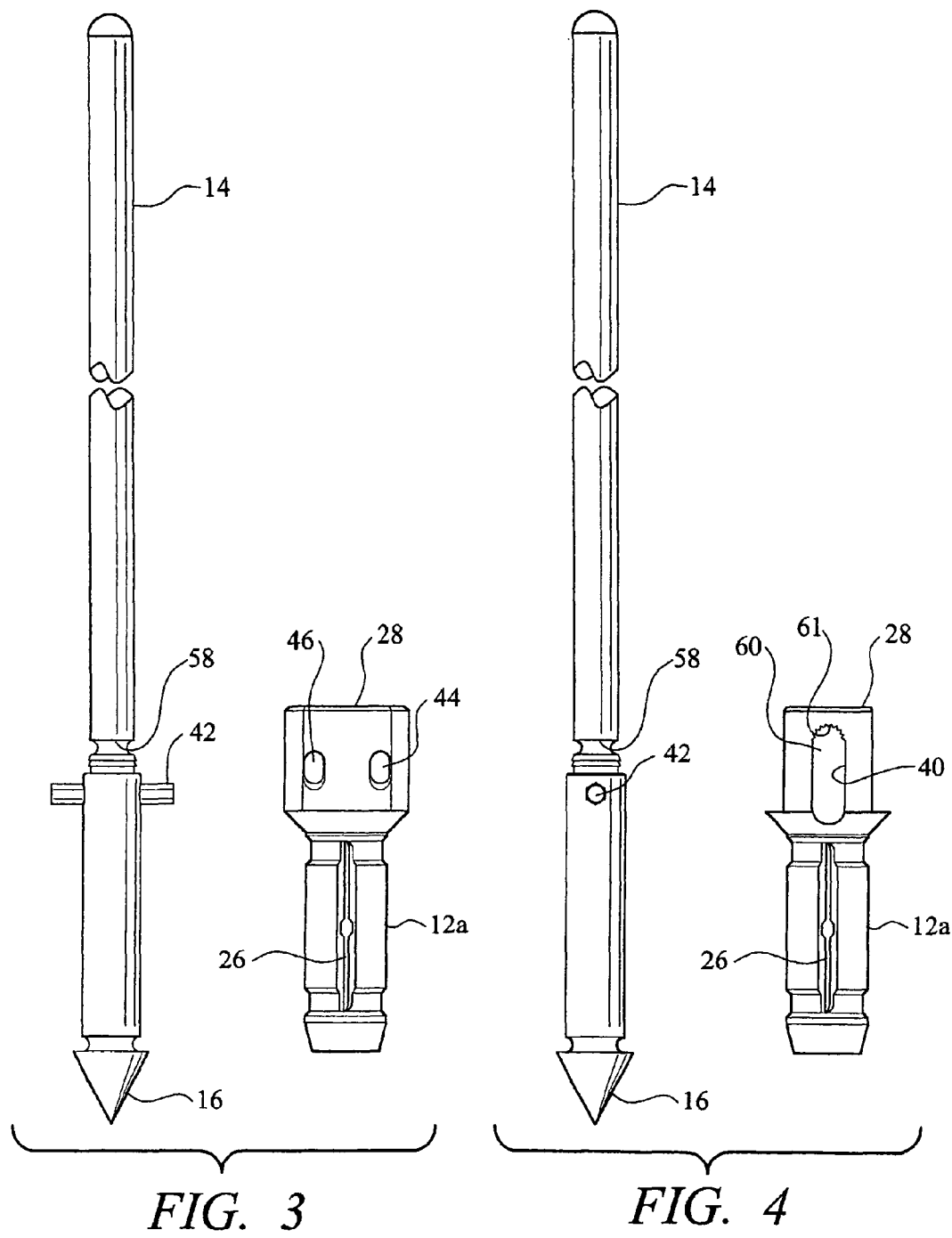
FIG. 3 is an exploded view in side elevation of this invention viewing the details of this invention with a view of the locking pin.
FIG. 4 is an exploded view in side elevation identical to the apparatus depicted in FIG. 3 rotated 90 degree.
Figure 7:
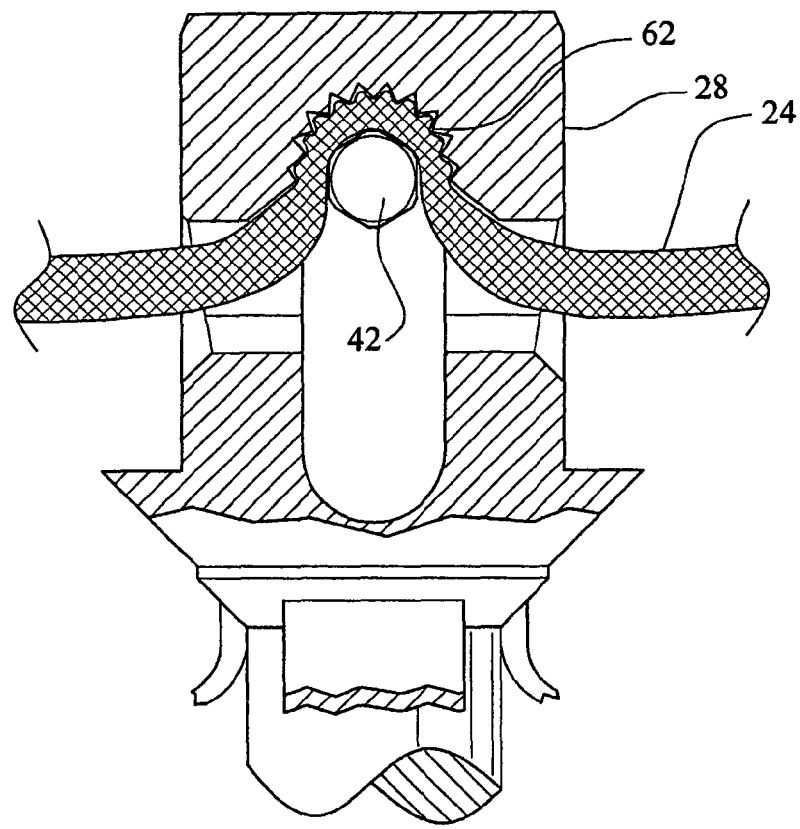
FIG. 7 is an enlarged fragmentary view illustrating the suture being locked into place in the apparatus of this invention.
Figure 8:
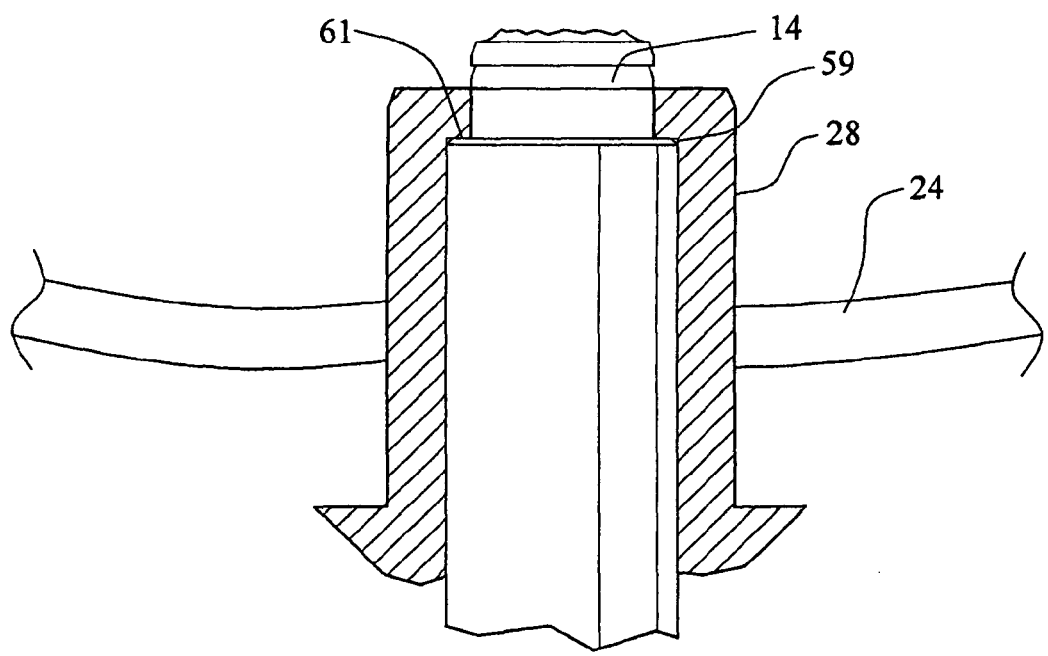
FIG. 8 is an enlarged fragmentary view identical to the apparatus depicted in FIG. 7 illustrating the removal of the working shaft.

FIGS. 3 and 4 are essentially exploded views showing both the frangible shaft 14 and the present invention attached to the anchor portion 12*a*. The frangible shaft 14 which is almost identical to the heretofore known anchor shafts is modified to include a drilled hole 52 adapted to receive pin 56. The pin 42 fits into drilled hole 52 and projects beyond the diameter of the shaft 14 to engage the grooves 40. The distal end or tip 16 of the anchor shaft 14 is tapered into a sharp point to penetrate through the bone. An annular groove 58 cut into the shaft 14 makes the shaft frangible and allows the surgeon to sever the portion of the shaft that extends beyond the annular groove when it breaks off at this weakened joint. (This feature is typical in these prior art anchors). The main body 28 is shown as being affixed to the anchor port 12.

FIG. 4 is a view of the apparatus depicted in FIG. 3 rotated 90 degrees to show the groove 40 formed in the body 28. Identical grooves 40 are formed on diametrically opposed walls of body 28 and define a camming surface for guiding the pin 42 as it is translated axially. To assemble the anchor 12 and the suture locking mechanism 10, the shaft 14 is inserted through the hollow central portion of the body 28 and the anchor portion 12*a* and suitably affixed thereto. The drilled hole being 52 oriented to align with the groove 40, thereafter, the pin 42 is inserted through drilled hole 52 so that the projection at either end thereof will extend into the opposing grooves 40.

Figure 9:
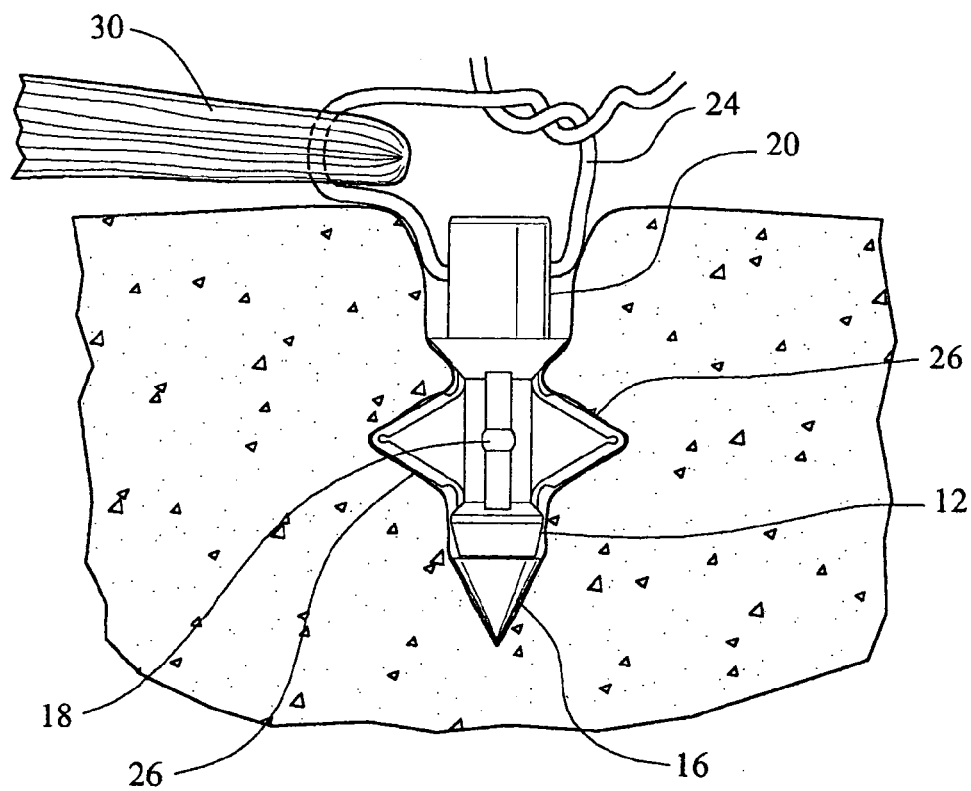
FIG. 9 is a schematic and elevation view of a prior art anchor and suture illustrating the tying of tissue to the bone.
Figure 10:
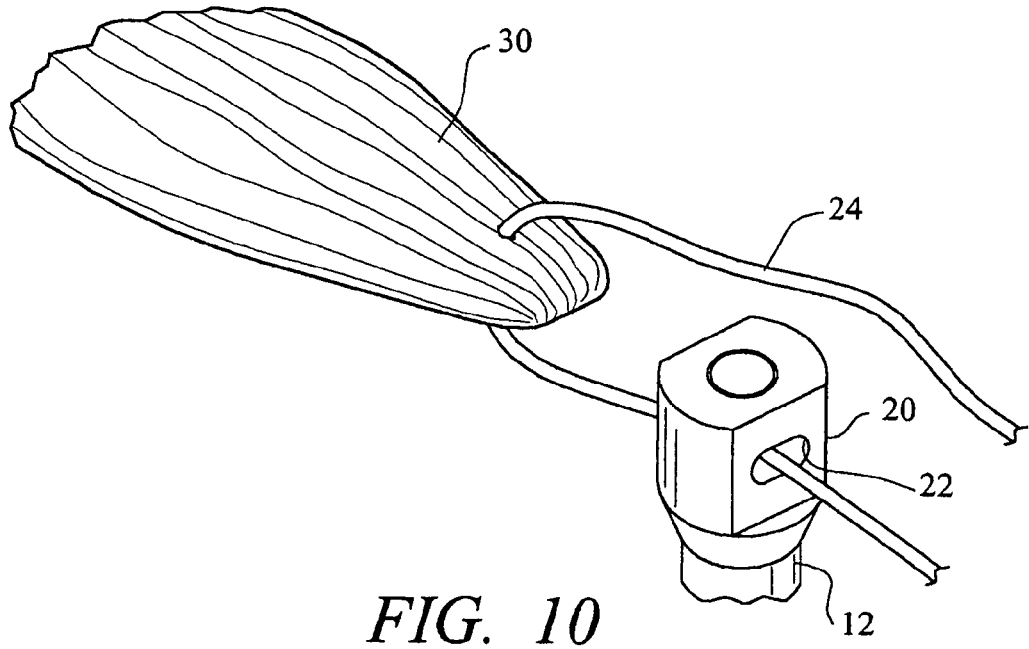
FIG. 10 is a perspective view illustrating the prior art method of threading of the suture to the tissue of the illustration depicted in FIG. 9.
Figure 11:
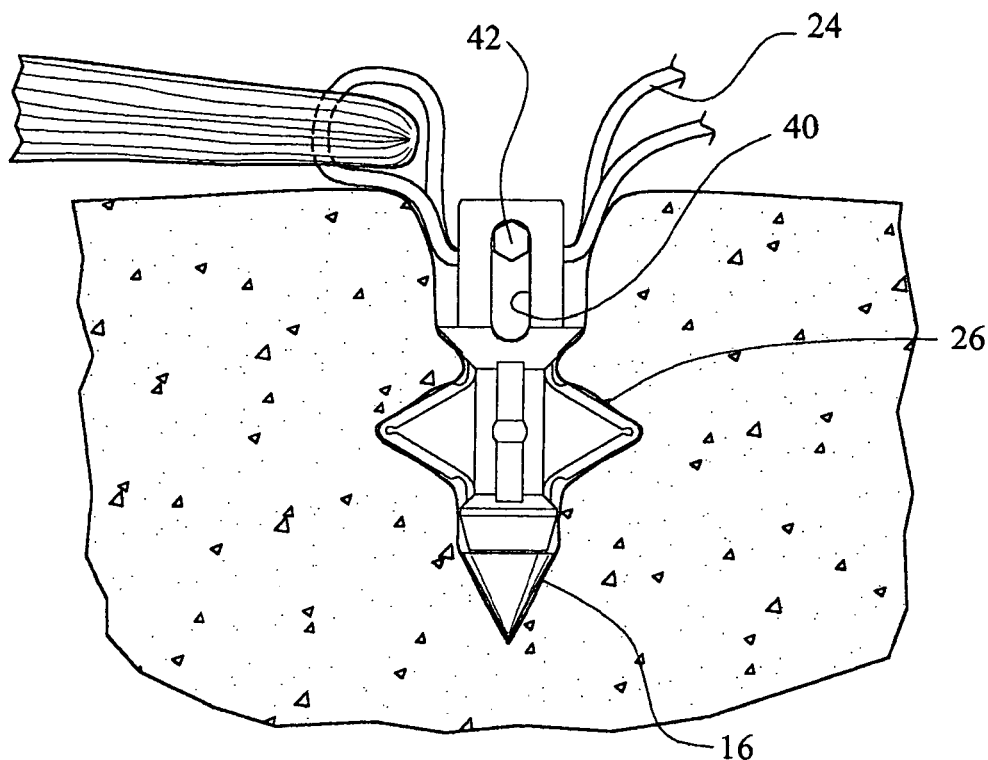
FIG. 11 is a schematic and elevation view of the present invention illustrating the threading of the suture to the anchor for tying the tissue to the bone.
Figure 12:
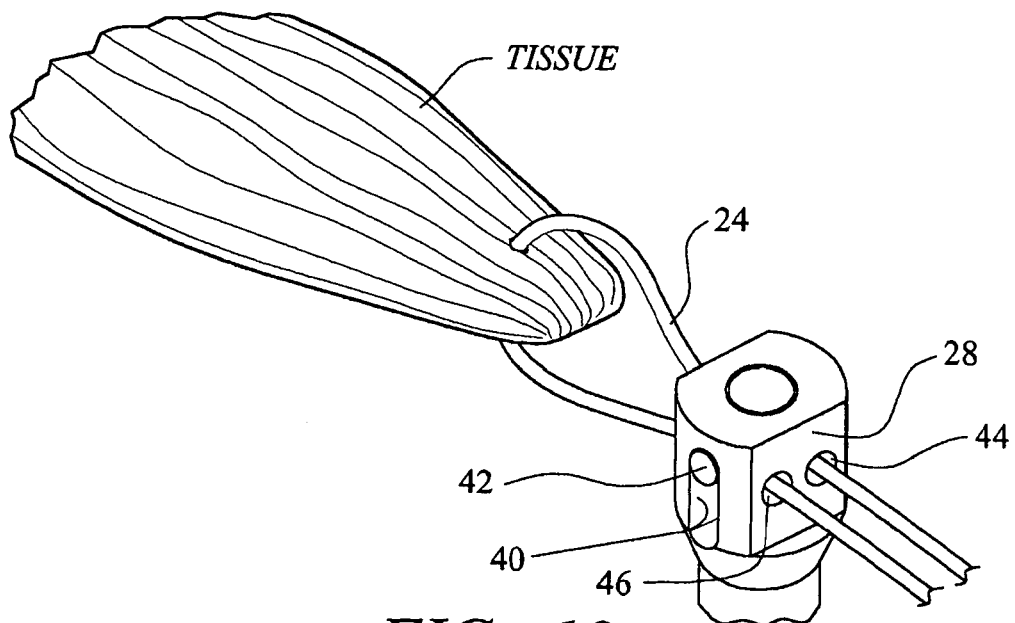
FIG. 12 is a view in perspective depicting the elements in FIG. 11 for illustrating the threading of the suture to the device of the present invention.
Figure 13:
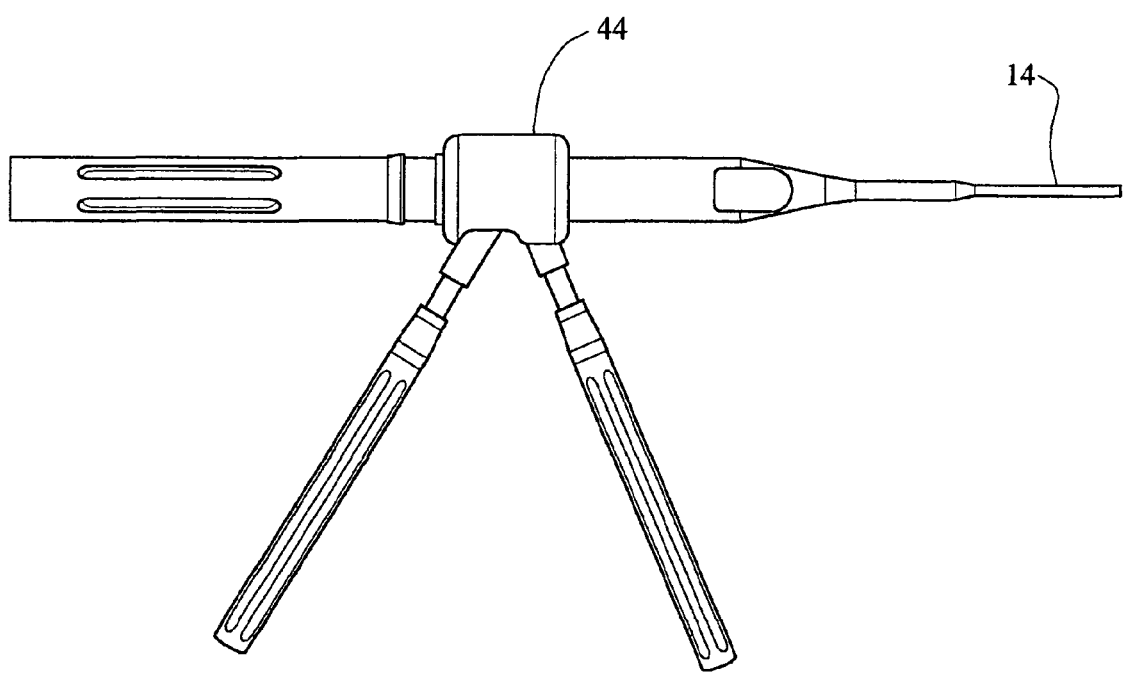
FIG. 13 is a plan view of a prior art medical instrument for inserting the anchor into the bone.

In performing the surgical procedure, after the cut is made into the skin of the patient and the tendon or tissue and bone are exposed, the surgeon with the use of an arbor, drill or the like will score the bone to form a starting hole for the anchor. The shaft 14 of the anchor is then installed in a well known manner using a mechanical power driving instrument or tool 41 (see FIG. 13) sometimes referred to as "FASTENATOR" and is available from THE ANSPACH EFFORT, INC, the assignee. As will be described in greater detail hereinbelow, tool 4*l* allows the surgeon to drive the anchor into the bone as shown in FIGS. 9 and 11 and automatically tie and lock the suture in place.

When the surgeon has completed the medical procedure and needs to apply the suture, the surgeon will thread the suture through the tissue and through the body 10 of the anchor by inserting the suture reaches through the apertures 44 and 46. As seen in FIGS. 1, 2, 5A, 5B, and 5C, the suture forms a loop enveloping the portion of the body being tied and the loops becomes tightened and sometimes closed as the suture proceeds into the suture locking mechanism. The surgeon will draw the suture reaches and force the loop toward the central opening in body 28 causing the suture and suture locking device to be drawn as closed to the tissue and bone as is possible as is demonstrated in FIGS. 5A, 5B, 5C, 7 and 8. While the surgeon is tightening the suture the surgeon starts squeezing the handle of the instrument 41. The deployment of the tool 41 driving the anchor into the bone forces the shaft 14 in the upward direction as shown in FIG. 5B. The action of the tool 41 forces the pin to ride in the grooves 40 as it proceeds toward the top of the main body 28 until it fits into the recess 62. The top surface 61 of recess 62 may be serrated as shown by reference numeral 64 so that when the pin is moved to its most upward position the suture reaches are forced against the serrated surface 61 where the force of the pin binds the surface of the suture against the serration, squeezing the suture therein so as to tie and lock the suture in place without the necessity of having the surgeon knot the suture. It should be appreciated that the pin is drawn into the locking position by the action of the tool 41. Hence, when tying tissue to tissue, for example, the suture locking mechanism can be utilized without the anchor being attached thereto.

As shown in FIG. 6 the pin 42 is contoured in a polygon shape, say hexagon, in this embodiment for the purpose to be described herein. The purpose of this shape is to assure that when in the locking position the side edges of the pin 42a and 42b lie parallel to the wall defining groove 62 so that the pin/wall won't bind against the suture and weaken the same.

As noted in FIGS. 5B and 5C, when the anchor is deployed the shaft is raised beyond the top edge 66 of the body 28 and exposes the annular groove 58. The outer edge 59 formed at the larger diameter of the shaft, at this juncture of the operation bears against the shoulder 61 formed on the inner face of the body 28. By bending the shaft 14, the shaft will break at this location (annular groove) and become severed from the anchor and body 28 and, then, discarded. By virtue of this invention the suture is locked into place by the inventive suture lock of this invention and by the fact that in the process of locking the suture the surgeon is being tightened relative to the bone so that the tissue is positioned as close to the bone as possible. Because the hand tying of the knot that was the heretofore practice is eliminated by virtue of this invention, the surgeon has the ability to pull on the suture to cause the tissue to cling to the bone (cinch) and then lock the suture in place when the surgeon is satisfied that this is the optimum position without incurring any backlash. In other words, this invention eliminates the slack that typically occurs when the suture is tied by hand.

Although this invention has been shown and described with respect to detailed embodiments thereof, it will be appreciated and understood by those skilled in the art that various changes in form and detail thereof may be made without departing from the spirit and scope of the disclosed invention.

It is claimed:

1. A suture locking device for securing and locking the ends of suture, said suture locking device having a cylindrical shaped body having a wall defining a cavity, a top portion and a side portion,
a pin laterally disposed in said cavity, said wall defining a recess formed in said body adjacent to the top portion and being in axial alignment with said pin, openings formed in said side wall portion in said suture locking device for accepting reaches of said suture intended to be tied so as to extend said suture intended to be tied laterally in said cavity to lie between said pin and said recess wall, wherein said side wall portion further comprises diametrically disposed axial slots angularly disposed from said openings, wherein said pin extends in said diametrically disposed axial slots;
said suture reaches in said cavity being urged against said recess wall and said pin upon deployment of said suture locking device whereby said suture is locked in place owing to the squeezing force exerted on said suture reaches by said pin against said recess wall.

2. A suture locking device as claimed in claim 1 wherein said pin is polygonal in shape.

3. A suture locking device as claimed in claim 2 wherein said recess wall is serrated.

4. A suture locking device as claimed in claim 3 wherein the flat portion of the polygonal shaped pin is located adjacent the wall portion of said recess extending normal relative to said serrations.

* * * * *